United States Patent [19]

Sandler et al.

[11] Patent Number: 4,486,551
[45] Date of Patent: Dec. 4, 1984

[54] METHOD OF PREPARING A FLAME RETARDED POLYURETHANE USING A FLAME RETARDED HALOGENATED POLYOL

[75] Inventors: Stanley R. Sandler, Springfield; Joseph M. Bohen, King of Prussia, both of Pa.

[73] Assignee: Pennwalt Corporation, Philadelphia, Pa.

[21] Appl. No.: 472,828

[22] Filed: Apr. 18, 1983

Related U.S. Application Data

[62] Division of Ser. No. 294,699, Aug. 20, 1981, Pat. No. 4,393,248.

[51] Int. Cl.³ .............................................. C08G 18/14
[52] U.S. Cl. ...................................... 521/171; 528/70; 528/76; 528/77

[58] Field of Search .................... 521/171; 528/70, 76, 528/77

[56] References Cited

U.S. PATENT DOCUMENTS 3,576,906  4/1971  Hickner et al. ..................... 521/171

*Primary Examiner*—Maurice J. Welsh

[57] ABSTRACT

A flame retardant, halogenated polyol having the formula

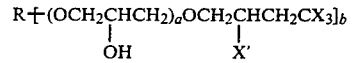

wherein R is an aliphatic radical substituted with at least 2 hydroxyl groups, X is a halogen, and X' is a halogen or hydrogen, is used in the reaction mixture for preparing flame retarded polyurethanes.

7 Claims, No Drawings

METHOD OF PREPARING A FLAME RETARDED POLYURETHANE USING A FLAME RETARDED HALOGENATED POLYOL

This application is a division of application Ser. No. 294,699, filed Aug. 20, 1981 and now U.S. Pat. No. 4,393,248.

BACKGROUND OF THE INVENTION

The present invention pertains to flame retardant halogenated polyols and more particularly to flame retardant tri- and tetrahalobutoxy polyols.

Polyurethanes are a widely used group of plastics in industry, having such applications as adhesives, as coatings, as insulators, as elastomers, as cushioning, as packaging materials, as potting resins, and the like. For many of these applications, it is desirable to incorporate a flame retardant into the polyurethane in order to reduce its flammability.

Two commercial, reactive, flame retardants that contain halogens are GAF's 2,3-dibromo-2-butenediol-1,4 and Olin's Thermolin RF-230, a chlorinated polyol. U.S. Pat. Nos. 3,919,166 and 4,022,718 describe GAF's product for use as a flame retardant for flexible polyurethane foam. U.S. Pat. Nos. 3,726,855; 3,741,921; and 3,847,844 describe Olin's Thermolin RF-230 product for use as a flame retardant for rigid polyurethane foam. None of these patents teaches the present invention.

SUMMARY OF THE INVENTION

The present invention is directed to a flame retardant polyol of the formula

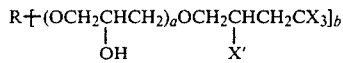   (I)

wherein
a is an integer of 0 or 1, with the proviso that
when a is 0, b is an integer of 1 to 8, R is selected from the group consisting of a substituted linear or branched alkyl of 1 to 12 carbons and a substituted cyclic alkyl of 3 to 12 carbons; X is selected from the group consisting of F, Cl, and Br; and X' is selected from the group consisting of H, F, Cl, and Br; whereby the substituent is selected from the group consisting of at least 2 hydroxyl groups, and when a is 1, b is an integer of 1 to 8, R is selected from the group consisting of hydrogen, a substituted linear or branched alkyl of 1 to 12 carbons and a substituted cyclic alkyl of 3 to 12 carbons; X is selected from the group consisting of F, Cl, and Br; and X' is selected from the group consisting of H, F, Cl, and Br; whereby the substituent is selected from the group consisting of at least 2 hydroxyl groups.

DETAILED DESCRIPTION OF THE INVENTION

The compositions of this invention are reactive flame retardant polyols that react with the isocyanates used in preparing the polyurethanes and thus become permanently bound to the polymer.

The compositions of this invention may be prepared by the addition of trihalomethanes or tetrahalomethanes to allyl ethers similar to the reactions described by Kharasch, Jensen and Urry in J. Am. Chem. Soc., 69, 1100 (1947). The method of preparation of the composition of this invention is as shown by equation (1) below:

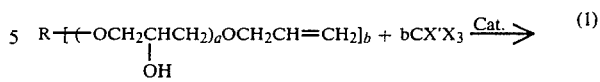   (1)

Formula I wherein a, b, X, X' and R are as previously defined.

Another method of preparing some of the compositions of this invention involves the reaction of trihalo or tetrahalobutoxyglycidyl ether with polyols as shown by equation (2) below:

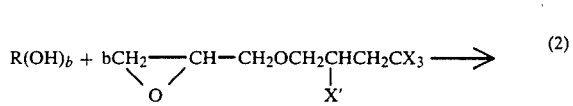   (2)

Formula I
(for the case where a = 1)

where a, b, X and X' are as defined earlier for Formula I.

The preparation of trichloro and tetrachlorobutoxyglycidyl ethers has been reported by Sadykhzade et al., in Chem. Absts. 85, 32717K (1976). However the reactions of tri- and tetrachlorobutoxyglycidyl ethers with polyols have not been described.

Representative polyols which may be used to form the compositions of this invention according to equation 2 include ethylene glycol, glycerol, trimethylolpropane, trimethylolethane, pentaerythritol, dipentaerythritol, dextrose, fructose, sorbitol, sucrose, etc.

The compositions may also be further reacted with various unsubstituted or halogen substituted epoxides to increase the molecular weight of the flame retardant and/or increase the halogen content. Epoxides useful for this purpose include ethylene oxide, propylene oxide, 3,3,3-trichloro-1,2-propylene oxide and 4,4,4-trichloro-1,2-butylene oxide.

The composition of this invention is used as flame retardants for polyurethane foams in the amount of from 5 to 100 parts of the polyol (php) component by weight to impart a measure of flame retardancy. The preferred loadings in rigid polyurethane foam is 25 to 100 php by weight.

Representative compositions of this invention where a of formula I is equal to zero are as follows: Note in the following structures that the letter Q is used as a shorthand way to illustrate the radical $$-CH_2CHCH_2CX_3$$
$$\phantom{-CH_2CH}|$$
$$\phantom{-CH_2CHCH_2C}X'$$

wherein X and X' are as previously defined.

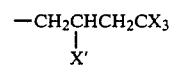

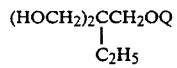

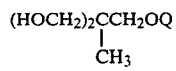

-continued
(HOCH$_2$)$_2$C(CH$_2$OQ)$_2$
(HOCH$_2$)$_3$CCH$_2$OQ

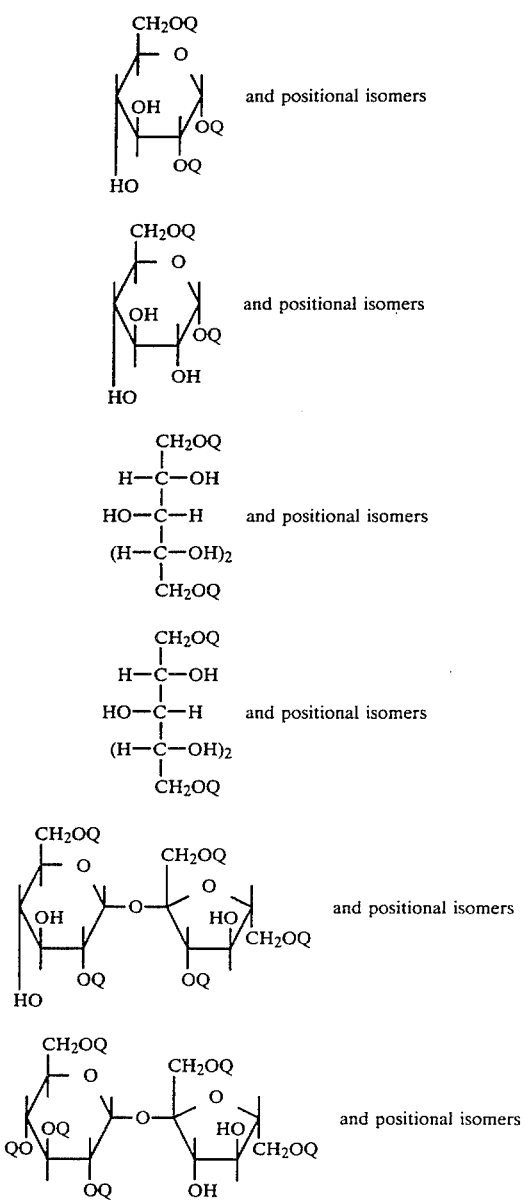
and positional isomers (×6)

Representative compositions of this invention where a of formula I is equal to one are as follows: Note in the following structures that the letter Y is used as a shorthand way to illustrate the radical

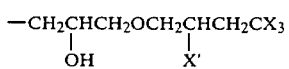

wherein X and X' are as previously defined.

HOY
HOCH(CH$_2$OY)$_2$
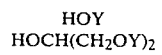
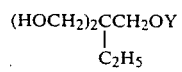

-continued
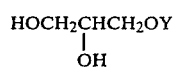

HOCH$_2$CHCH$_2$OY
|
OH (HOCH$_2$)$_2$C(CH$_2$OY)$_2$
(HOCH$_2$)$_3$C—CH$_2$OY

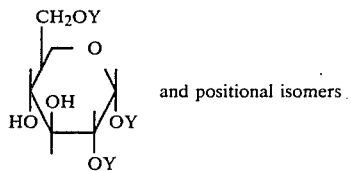
and positional isomers (×2)

CH$_2$OY
|
H—C—OY
|
YO—C—H      and positional isomers
|
(H—C—OY)$_2$
|
CH$_2$OY CH$_2$OY
|
H—C—OH
|
HO—C—H      and positional isomers
|
(H—C—OH)$_2$
|
CH$_2$OY CH$_2$OY
|
H—C—OY
|
HO—C—H      and positional isomers
|
(H—C—OY)$_2$
|
CH$_2$OY CH$_2$OY
|
H—C—OY
|
HO—C—H      and positional isomers
|
H—C—OY
|
H—C—OH
|
CH$_2$OY

YOCH(CH$_2$OY)$_2$

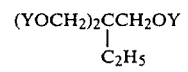

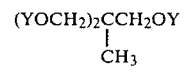

YOCH$_2$CHCH$_2$OY
|
OY

C(CH$_2$OY)$_4$
(YOCH$_2$)$_3$CCH$_2$OH

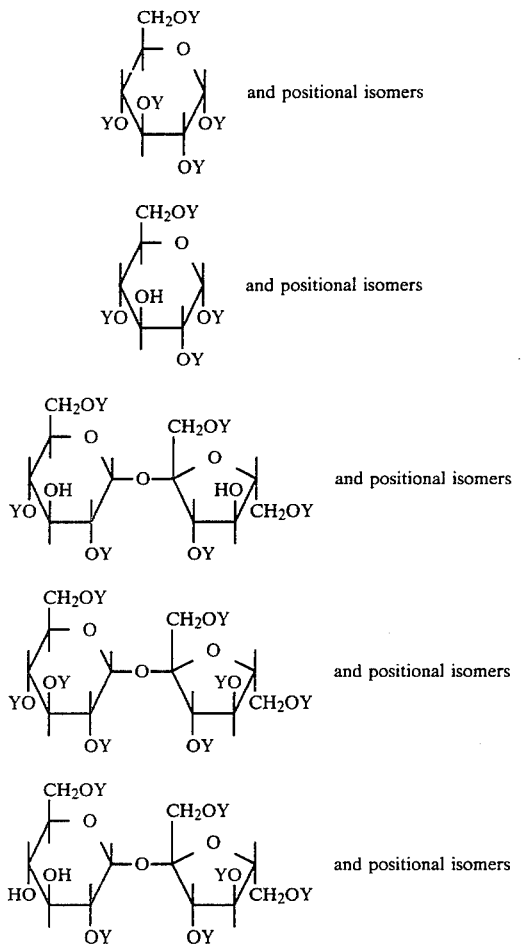

and positional isomers and positional isomers and positional isomers and positional isomers and positional isomers The preferred compositions of this invention for use as flame retardants in polyurethane foam are as follows:

(HOCH₂)₂CCH₂OQ
|
C₂H₅

(HOCH₂)₂C(CH₂OQ)₂
(HOCH₂)₃CCH₂OQ
(YOCH₂)₃CC₂H₅
(HOCH₂)₂C(CH₂OY)₂
(YOCH₂)₄C
HOCH(CH₂OY)₂
HOY

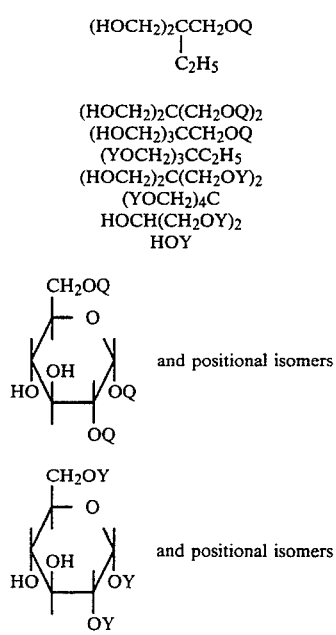

and positional isomers and positional isomers

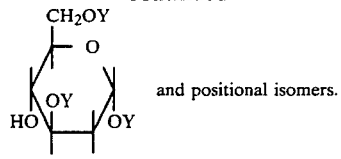

and positional isomers.

The more particularly preferred compositions of this invention are the above compositions wherein X and X' are Cl.

EXAMPLES

Polyurethane foam described in the following examples is made by dissolving the flame retardant additive in the polyol when used in less than 100 php followed by the addition of catalysts, surfactant, water, blowing agent and isocyanate. The mixture is stirred by a high-speed mixer and is poured into a container and allowed to rise. The foam is aged at least overnight, and preferably for seven days, before being cut into test sections for testing. The flame retardant properties are evaluated using ASTM D-1692-74.

EXAMPLE 1

To a 2-liter three-necked round-bottom glass reaction vessel equipped with a mechanical stirrer, condenser and addition funnel is added 250.0 g (1.4 moles) of trimethylolpropane monoallyl ether. Then 1250 g (6.3 moles) of bromotrichloromethane is added and the solution is stirred and refluxed (105° C.) for 6 hours. The excess bromotrichloromethane is removed to give 450.0 g (84.5% yield) of crude product.

The infrared spectrum is consistent with the assigned structure. The viscosity (cps) of this product was determined at 25° C. using a Capillary Viscometer according to the method of ASTM D-445; it was 2,278 cps.

An alternate procedure for this preparation involves adding trimethylolpropane monoallyl ether containing 10% dissolved AIBN [Azobisisobutyronitrile (called Vazo 64) from Dupont] and then adding it to a refluxing solution of bromotrichloromethane.

EXAMPLE 2

To a 12-liter three-necked flask equipped as in Example 1 is added 10,000 g (65.2 moles) of carbon tetrachloride which is heated to reflux. Then a solution of 100 g 2-t-butylazo-2-cyanobutane (Luazo 82 from Lucidol) in 1000 g (7.5 moles) of trimethylolpropane monoallyl ether is added portionwise over a period of 4 hours. After the addition the mixture is refluxed for another two hours and an additional 100 g of Luazo 82 is added. The reaction mixture is then stirred and refluxed for an additional 18 hours. The excess carbon tetrachloride is removed under reduced pressure to give 1750 g (93% yield) of crude product.

The infrared spectrum is consistent with the assigned structure. The viscosity, determined as in Example 1, was 11,385 cps.

EXAMPLE 3

To a 2-liter three-necked flask equipped as in Example 1 is added 2000 g (13 moles) of carbon tetrachloride which is heated to reflux. Then a solution of 20 g Luazo 82 (Lucidol) in 200 g (1.75 moles) of allyl glycidyl ether is added portionwise over a period of 4 hours. After an additional 2 hours of refluxing another 20 g of Luazo 82

(Lucidol) is added to the reaction mixture and refluxing continued for an additional 18 hours. The excess carbon tetrachloride and allyl glycidyl ether are removed under reduced pressure to give 394.3 g (84% yield) of crude product.

The infrared spectrum is consistent with the assigned structure.

EXAMPLE 4

To a 2-liter three-necked flask equipped with a mechanical stirrer, condenser, heating mantle with temperature controller, addition funnel, and a nitrogen inlet-outlet are added 128.8 g (1.4 moles) of glycerol and 7.5 g (0.053 mole) of boron trifluoride etherate. The reaction mixture is heated to 90°–100° C. and 750.4 g of the product from Example 3 (approximately 2.8 moles) is added over a 35 minute period without external heating. An exotherm was noted in which the temperature rose to 106° C. After the exotherm ceases the reaction mixture is heated at 90° C. for a total reaction time of 3½ hours.

EXAMPLE 5

To a reaction flask as described in Example 4 are added 13.6 g (0.1 mole) of pentaerythritol, and 9.2 g (0.1 mole) ethylene glycol. Then 10 drops (0.0028 mole) of boron trifluoride etherate is added and the reaction mixture heated to 100° C. The product of Example 3 (107.2 g, approximately 0.4 mole) was added in about 1 hour. The reaction mixture is maintained at 100° C. for 6 hours. The temperature is then raised to 110°–130° C. for 24 hours.

EXAMPLE 6

To a 5-liter three-necked flask equipped as in Example 1 is added 3200 g (16.0 moles) of bromotrichloromethane which is heated to reflux. Then a solution of 1.0 g of azobis(isobutyronitrile) (Vazo 64 from DuPont) in 365.3 g (3.2 moles) of allyl glycidyl ether is added portionwise over a 4-hour period. The reaction mixture is stirred and refluxed for a total of 24 hours and then the excess bromotrichloromethane is removed under reduced pressure to give 1000 g (100% yield) of product.

The infrared spectrum is consistent with the assigned structure.

EXAMPLE 7

To a 250 ml reaction flask equipped as in Example 1 are added 13.7 g (0.1 mole) of allyl glycerol, 1.0 g of azobis(isobutyronitrile) (Vazo 64 from DuPont), and 68.5 g (0.35 mole) of bromotrichloromethane. The reaction mixture is refluxed for 17 hours and then the unreacted starting material is stripped-off under reduced pressure to give 29.0 g (87% yield) of product.

The infrared spectrum is consistent with the assigned structure.

EXAMPLE 8

To a 5-liter three-necked reaction flask equipped as described in Example 1 is added 3960 g (19.9 moles) of bromotrichloromethane which is heated to reflux. Then a solution of 4.8 g of Vazo 64 in 792.0 g (6.0 moles) of allyl glycerol is added over a 4-hour period. The unreacted starting material is then removed under reduced pressure to give 1823 g of product (87% yield).

The determined infrared spectrum was consistent with the assigned structure.

The composition of Example 7 or 8 may also be obtained by the acidic hydrolysis of the composition of Example 6.

EXAMPLE 9

To a 12-liter three-necked reaction flask equipped as described in Example 1 is added 5994 g (38.9 moles) of carbon tetrachloride which is heated to reflux. Then a solution of 60 g of Luazo 82 in 599.4 g (5.26 moles) of allyl glycerol is added dropwise over a period of 5 hours. Then an additional 60 g of Luazo 82 is added and the mixture refluxed for 17 hours. The unreacted starting materials are removed under reduced pressure to give 1224.2 g (87% yield) of crude product.

The infrared spectrum is consistent with the assigned structure. The viscosity, determined as in Example 1, was 1,886 cps.

The composition of Example 9 may also be obtained by the acid-catalyzed hydrolyses of the composition of Example 3.

EXAMPLE 10

To a 500 ml reaction flask equipped as described in Example 1 is added 100 g (0.84 mole) of chloroform which is heated under reflux. Then a solution of 0.5 g of Vazo 64 dissolved in 10 g (0.09 mole) of allyl glycidyl ether is added dropwise over a period of 1 hour. The reaction mixture is refluxed for 24 hours and then concentrated under reduced pressure to give the intermediate product. Acid catalyzed hydrolysis of this intermediate gives the desired final product.

EXAMPLE 11

To a 500 ml stirred autoclave are added 160 g (0.43 moles) of the composition of Example 1 and 10 drops of boron trifluoride etherate. Then the reaction mixture is heated to 100° C. and 40 g (0.69 moles) of propylene oxide is slowly added (1 hr). The reaction mixture is maintained at 100° C. for 6 hours and then cooled to room temperature to give the product in almost quantitative yield.

EXAMPLES 12–18

A rigid polyurethane foam was prepared using the compositions of Examples 1, 2, 4, 7 or 8, and 9 and its flame retardant properties compared to a foam containing no flame retardant additives. These results are shown in Table 1.

TABLE 1

| COMPOSITION | EXAMPLE 12 | EXAMPLE 13 | EXAMPLE 14 | EXAMPLE 15 | EXAMPLE 16 | EXAMPLE 17 | EXAMPLE 18 |
|---|---|---|---|---|---|---|---|
| Composition of Example 1 | 60.0 | — | — | — | — | — | 16.0 |
| Composition of Example 2 | — | 96.5 | — | — | — | — | — |
| Composition of Example 4 | — | — | 100.0 | — | — | — | — |
| Composition of Examples 7 or 8 | — | — | — | 54.2 | — | — | — |
| Composition of Example 9 | — | — | — | — | 100.0 | — | — |
| Polyol Poly G 71-530 (Olin) | 40.0 | 3.5 | — | 45.8 | — | — | — |

TABLE 1-continued

| COMPOSITION | EXAMPLE 12 | EXAMPLE 13 | EXAMPLE 14 | EXAMPLE 15 | EXAMPLE 16 | EXAMPLE 17 | EXAMPLE 18 |
|---|---|---|---|---|---|---|---|
| Polyol Multranol E-9221 (Mobay) | — | — | — | — | — | 100.0 | 84.0 |
| Silicone Surfactant DC 193 (Dow Corning) | 1.5 | 1.5 | 1.5 | 1.5 | 1.5 | 1.8 | 1.8 |
| Catalyst Polycat 8 (Abbott) | 1.0 | 1.3 | 1.1 | 1.0 | 1.3 | 1.0 | 1.0 |
| Catalyst T12 (M & T) | 0.05 | — | 0.05 | 0.05 | — | 0.1 | 0.1 |
| Blowing Agent Isotron 11 (Pennwalt) | 30.0 | 33.0 | 33.0 | 30.0 | 30.0 | 36.0 | 33.0 |
| Isocyanate Mondur MR (Mobay) | 119.0 | 95.0 | 99.0 | 128.4 | 135.0 | 125.6 | 120.1 |
| NCO/OH Index | 1.15 | 1.15 | 1.15 | 1.15 | 1.15 | 1.10 | 1.10 |
| FLAME RETARDANT PROPERTIES: | | | | | | | |
| ASTM D-1692 | | | | | | | |
| Extent of Burn (inches)* | 0.5 | 0.6 | 0.5 | 0.5 | 0.5 | 5.0 | 3.2 |
| Rate of Burn (inches/min) | 0.9 | 1.3 | 1.0 | 1.1 | 0.9 | 5.0 | 2.7 |

*5 inches = Total Sample

Example 17 shows that without flame retardant additives this rigid polyurethane foam is totally consumed (5 inches total length of sample) in the ASTM D-1692 test. Example 18 shows that when 16 parts of the composition from Example 1 is incorporated into a similar rigid polyurethane foam formulation, the flame retardancy is markedly increased. When 60 parts of this same composition was used the resulting foam was flame retardant to a much greater extent and burned only 0.5 inch (Example 12).

EXAMPLE 19

A rigid polyurethane foam is prepared using the composition of Example 5 in place of the composition of Example 4 in Example 14 of Table 1. The observed flame retardancy is equivalent to that found for Example 14.

What is claimed:

1. A flame retarded polyurethane prepared from a reaction mixture which comprises an isocyanate, a catalyst, a surfactant, water, a blowing agent, and 5 to 100 parts per hundred parts polyol by weight of a composition having the formula $$R \!\!-\!\!\!\left[(OCH_2\underset{\underset{OH}{|}}{C}HCH_2)_a OCH_2\underset{\underset{X'}{|}}{C}HCH_2CX_3\right]_b$$

wherein
a is an integer of 0 or 1, with the proviso that
when a is 0, b is an integer of 1 to 8, R is selected from the group consisting of a substituted linear or branched alkyl of 2 to 12 carbons and a substituted cyclic alkyl of 3 to 12 carbons, X is selected from the group consisting of F, Cl, and Br, and X' is selected from the group consisting of H, F, Cl, and Br, whereby the substituent is selected from the group consisting of at least 1 hydroxyl groups, and
when a is 1, b is an integer of 1 to 8, R is selected from the group consisting of hydrogen, a substituted linear or branched alkyl of 1 to 12 carbons and a substituted cyclic alkyl of 3 to 12 carbons, X is selected from the group consisting of F, Cl, and Br, and X' is selected from the group consisting of H, F, Cl, and Br, whereby the substituent is selected from the group consisting of at least 2 hydroxyl groups.

2. The composition of claim 1 wherein a=0, b=1, $$R = (HOCH_2)_2\underset{\underset{C_2H_5}{|}}{C}\!\!-\!\!CH_2\!-\!,$$

X'=Br, and X=Cl.

3. The composition of claim 1 wherein a=0, b=1, $$R = (HOCH_2)_2\underset{\underset{C_2H_5}{|}}{C}\!\!-\!\!CH_2\!-\!,$$

and X' and X are Cl.

4. The composition of claim 1 wherein a=0, b=1, $$R = CH_2\!\!-\!\!\underset{\underset{OH}{|}}{C}H\!\!-\!\!CH_2\!-\!,$$
$$\phantom{R = }\overset{|}{OH}$$

X'=Br, and X=Cl.

5. The composition of claim 1 wherein a=0, b=1, $$R = CH_2\!\!-\!\!CH\!\!-\!\!CH_2\!-\!$$
$$\phantom{R = }\overset{|}{OH}\ \overset{|}{OH}$$

and X and X' are Cl.

6. The composition of claim 1 wherein a=1, b=2, $$R = HOCH\underset{\diagdown}{\overset{\diagup CH_2-}{\phantom{X}}}_{CH_2-}$$

and X=X'=Cl.

7. The composition of claim 1 wherein a=0, b=1, X'=H, X=Cl and $$R = CH_2\!\!-\!\!CH\!\!-\!\!CH_2\!-\!.$$
$$\phantom{R = }\overset{|}{OH}\ \overset{|}{OH}$$

* * * * *